(12) United States Patent
Trautwein

(10) Patent No.: US 8,443,679 B2
(45) Date of Patent: May 21, 2013

(54) TESTING DEVICE WITH A DRIVE, WHICH CONVERTS ROTATIONAL MOVEMENT INTO A RECIPROCATING MOVEMENT OF VARIABLE AMPLITUDE

(76) Inventor: Frank Thilo Trautwein, Filderstadt (DE)

( * ) Notice: Subject to any disclaimer, the term of this patent is extended or adjusted under 35 U.S.C. 154(b) by 457 days.

(21) Appl. No.: 12/673,589

(22) PCT Filed: Aug. 14, 2007

(86) PCT No.: PCT/EP2007/007157
§ 371 (c)(1),
(2), (4) Date: Feb. 16, 2010

(87) PCT Pub. No.: WO2009/021534
PCT Pub. Date: Feb. 19, 2009

(65) Prior Publication Data
US 2011/0016983 A1    Jan. 27, 2011

(51) Int. Cl.
*G01N 3/10*    (2006.01)
*G01N 3/08*    (2006.01)

(52) U.S. Cl.
USPC .............................................. 73/825; 73/826

(58) Field of Classification Search
USPC ................... 73/808, 806, 813, 814, 815, 816, 73/818, 825, 826, 831
See application file for complete search history.

(56) References Cited

U.S. PATENT DOCUMENTS

| | | | | |
|---|---|---|---|---|
| 2,215,958 A | * | 9/1940 | Fullerton | 73/808 |
| 2,806,431 A | * | 9/1957 | Woydt | 91/353 |
| 3,103,173 A | * | 9/1963 | Griswold | 417/405 |
| 3,162,131 A | * | 12/1964 | Clark | 417/364 |
| 4,255,989 A | * | 3/1981 | Dinelli | 74/831 |

FOREIGN PATENT DOCUMENTS

| | | | |
|---|---|---|---|
| FR | 1388925 A | * | 2/1965 |
| GB | 450347 A | * | 9/1973 |

* cited by examiner

*Primary Examiner* — Andre Allen
*Assistant Examiner* — Jonathan Dunlap
(74) *Attorney, Agent, or Firm* — Mark Levy; Hinman, Howard & Kattell, LLP

(57) ABSTRACT

The invention relates to a testing device for the static and dynamic testing of workpieces, comprising a first clamping device and a second clamping device for the workpiece, and a drive for the cyclical displacement of the second clamping device, wherein the drive has a rocker arm on which the second clamping device is pivotably mounted and the two ends of the rocker arm are connected in each case to a pivotably mounted link, and the free ends of the links are coupled in each case to a crank drive, wherein the links protrude from the ends of the rocker arm in the same direction in the basic position of the testing device.

16 Claims, 8 Drawing Sheets

TESTING DEVICE WITH A DRIVE, WHICH CONVERTS ROTATIONAL MOVEMENT INTO A RECIPROCATING MOVEMENT OF VARIABLE AMPLITUDE

RELATED APPLICATION

This patent application claims priority to PCT application number PCT/EP2007/007157, filed Aug. 14, 2007.

BACKGROUND OF THE INVENTION

1. Field of the Invention

The invention relates to test devices and, more particularly, to a test device for static and dynamic testing of workpieces.

The invention relates to a test device for the static and dynamic testing of workpieces, having a first, fixed clamping device and a second, movable clamping device for the workpiece, and a drive for moving the second clamping device, where the drive has a rocker on which the second clamping device is mounted in a rotatable manner, and the two ends of the rocker are each connected to a rotatably mounted connecting rod, and the free ends of the connecting rods are each coupled to a crank mechanism.

The test machine is based on the principle of the generation of a stroke by means of a crank mechanism. Since the stroke has to be controlled continuously during operation for some component tests and therefore must be adjustable, a simple means of adjustment during running operation, which in addition is as far as possible free from wear, is necessary.

A means of adjusting the amplitude during operation is known from GB450,347. In this device, a rocker is driven by two cams. Adjustment of the phase position of the cams with respect to one another gives rise to different strokes, from 0 to twice the throw of the cams. A disadvantage in this arrangement is the necessity for slide blocks. These have to support the counterpressure, and are at the same time subject to a significant relative movement during each stroke, meaning that high wear can be expected.

2. Discussion of the Prior Art

This problem of the basic principle was recognized, for example, in FR1388925 and overcome by making the connection to the rocker by means of two connecting rods. However, this mechanism has the disadvantage that it is not possible to produce strokes which are as small as desired therewith. This is necessary on the one hand for "starting" a test machine, since otherwise it may not be possible to apply the required drive energy of the drive in order to subject the sample to the desired load, and on the other hand the smallest possible stroke may already be so large that it overloads the sample.

The problem of a stroke which cannot be set to zero has been solved by DE2900373C3 by using a total of four further connecting rods or push rods. Although this enables the stroke to be reset to zero, a special geometrical matching of the dimensions is necessary for the principle shown. The large number of joints and components used (and thus of the masses moved) means that the principle appears of little suitability for a cyclic application which is intended to be operated for many years without play and wear.

SUMMARY OF THE INVENTION

The invention therefore has the object of providing a test device which has a simple construction, has low energy consumption, is subject to low wear and in which a stroke amplitude between zero and a maximum value can be set and controlled during operation.

This object is achieved in accordance with the invention by means of a test device of the type mentioned at the outset in which the drive connecting rods project from the ends of the rocker in the same direction in the starting position of the test device.

In accordance with the invention, the crank mechanisms are arranged on opposite sides of the rocker. This arrangement means that the requirement for the connecting rods to project from the ends of the rocker in the same direction is achieved in a simple manner.

The rocker is thus driven from both sides by means of connecting rods, which, in the starting position of the test device, are arranged equally on the rocker, i.e. are at the same angle to the rocker. The test device according to the invention has the essential advantage that it has exclusively pivot bearings and therefore slide blocks, which are subject to very high wear, are not required. In addition, setting to zero stroke is possible. Finally, only a small number of components is needed, restricted to the rocker, the two connecting rods and the two crank mechanisms.

The test device according to the invention has very low energy consumption compared with servo-hydraulic or servo-pneumatic test machines, since hydraulic devices have high power losses in servo valves, causing the hydraulic medium to heat up, requiring further supply of energy for cooling thereof. In addition, hydraulic units must be designed for the maximum capacity of the load frame and of the hydraulic cylinders driven thereby, and consequently they do not work efficiently in the case of moderate and small test loads or test displacements. The generation of compressed air for servo-pneumatic systems is likewise inefficient, predominantly owing to the generation of heat in the compressor.

The parts used for the test device according to the invention are manufactured in large number for standard applications and have a simple design. Furthermore, the choice of the test parameters, such as the frequency, load and distance, is absolutely flexible and not tied to resonance frequencies, as is often the case in other test machine designs. Since all components are connected to one another via flexurally soft bearings or pivot bearings, a forcible control is given. The dynamics (acceleration, force/distance) during cyclic testing can thus be set to higher values than is possible in the case of machines having a magnetic linear drive.

Owing to the system-inherent inertness and design conversion of the rotational movement into a stroke movement, very simple control or very high control quality of the input variables, such as, for example, force, elongation or displacement, is possible, including the case of samples which exhibit a highly non-linear force/displacement behavior.

In order to reduce the load on the joints of the individual components or in order to be able to increase the test frequency, the crank mechanism is designed with an adjustable cam, in particular with a twin cam. In order to be able to achieve very small amplitudes, the throw can optionally be set to such a small amplitude, or where required, up to twice the throw of this small amplitude, by adjusting the cam, in which case the fine adjustment is carried out by mutual angular adjustment of the crank mechanisms. The static adjustment by means of a twin cam is carried out, for example, by mutually adjusting two cams lying one inside the other, also enabling a zero stroke to be produced.

Since component testing is often carried out not only with an amplitude around the zero line, but additionally a prestress by means of which the component is then loaded with an amplitude, the drive is attached to a carriage and can be prestressed with tension or pressure in the sliding direction towards the second clamping device. This enables a base load to be applied in the form of a base tension or a pressure, by means of which the sample is then dynamically loaded (medium load with superimposed cyclic load). The forces here can be distributed in such a way that they are exclusively in the pressure region or in the tension region or tension and pressure forces are applied alternately.

Tensile experiments and fatigue tests can be carried out with the test device according to the invention in static and dynamic types of operation. Furthermore, the test device and the actuators can be set up and arranged flexibly, enabling arrangement in a load frame or mounting on a mounting plate.

It is furthermore possible to synchronize a plurality of devices through electronic synchronization of the drive motors with one another. This serves for multiaxial load application to samples.

In accordance with the invention, the carriage can be moved mechanically, for example by means of a threaded spindle or toothed rack, or hydraulically. For precise setting of this prestressing force, provision is made, for example, for a load cell, which is connected, in particular, to the sample.

A variant of the invention proposes that the workpiece is a sample or a hydraulic cylinder. By means of the hydraulic cylinder, the hydraulic medium can be applied, for example, to an external sample, which is loaded, for example, under varying internal pressure.

It is also possible for components to be tested with a external pressure by using a hydraulic cylinder to convert the mechanical drive into a hydraulic pressure, which is more energy-efficient than generation of pressure by means of a hydraulic unit and regulation by servo valve.

On the other hand, the hydraulic medium can be passed on to a second, external hydraulic cylinder, by means of which a poorly accessible or large component is loaded. By connecting a plurality of test devices together with hydraulic cylinders connected thereto in each case for transmission of force to a sample, forces can be applied in various directions in order, for example, also to test multiaxial load states.

Further areas of application for the device according to the invention are, inter alia, stamping machines, presses, pumps, vibrating screens, test machines for vibration testing or other oscillating equipment in which a means of adjusting the stroke amplitude during operation is necessary or advantageous.

Further advantages, features and details of the invention arise from the sub-claims and the following description, in which particularly preferred illustrative embodiments are described in detail with reference to the drawing. The features depicted in the drawing and mentioned in the description and in the claims may each be essential to the invention individually or in any desired combination.

DETAILED DESCRIPTION OF THE PREFERRED EMBODIMENT

Figure 1:
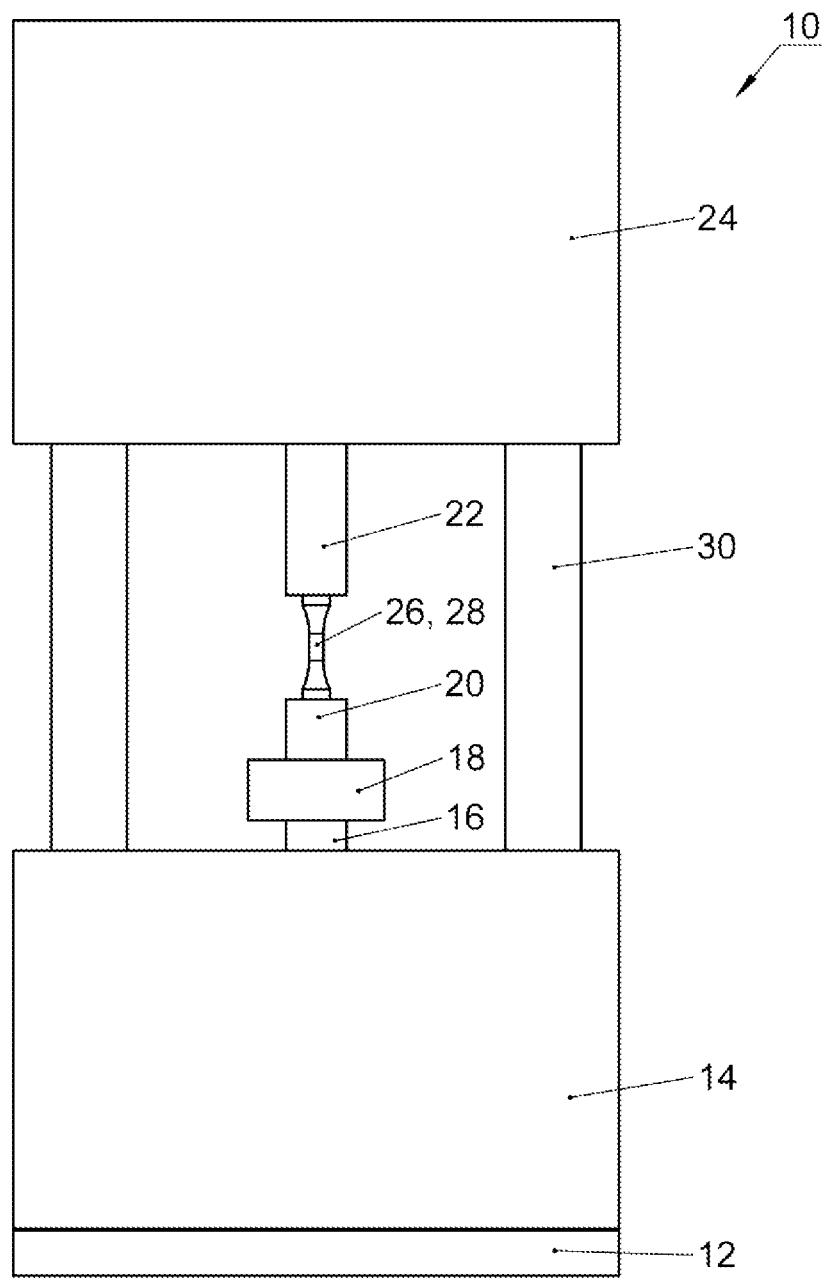
FIG. 1 shows a first variant of the test device according to the invention.

FIG. 1 depicts a first variant of a test device which is denoted in its entirety by 10, in which a first actuator 14 for a quasi-static stroke movement, i.e. for a mean-load setting, is provided in a machine stand 12. This first actuator 14 is connected via a rigid connection 16 to a force transducer 18, which ends in a first clamping device 20. This first clamping device 20 is located opposite a second clamping device 22, which is driven by a second actuator 24 for a cyclic (dynamic) stroke movement. A workpiece 26, in particular a sample 28, is clamped between the two clamping devices 20 and 22. The position of the actuator 24 is adjustable and fixable along the load frame 30, depending on the sample size.

Figure 2:
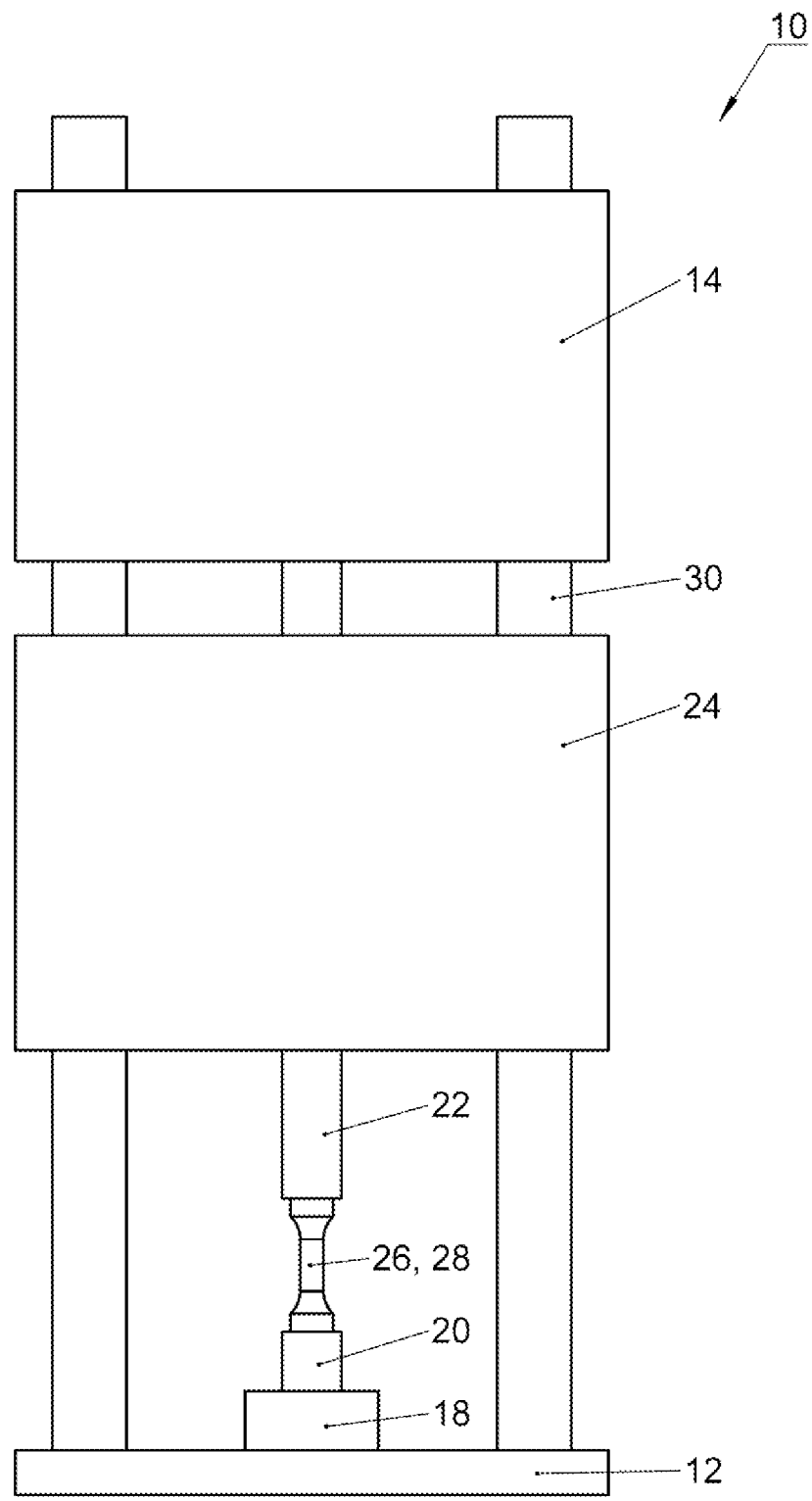
FIG. 2 shows a second variant of the test device according to the invention.

In the variant of the invention according to FIG. 2, the force transducer 18 is connected directly to the machine stand 12, where the second actuator 24 is arranged movably, by means of the first actuator 14, along the load frame 30 of the machine stand 12, causing a prestressing force or a pressure to be applied to the workpiece 26.

Figure 3:
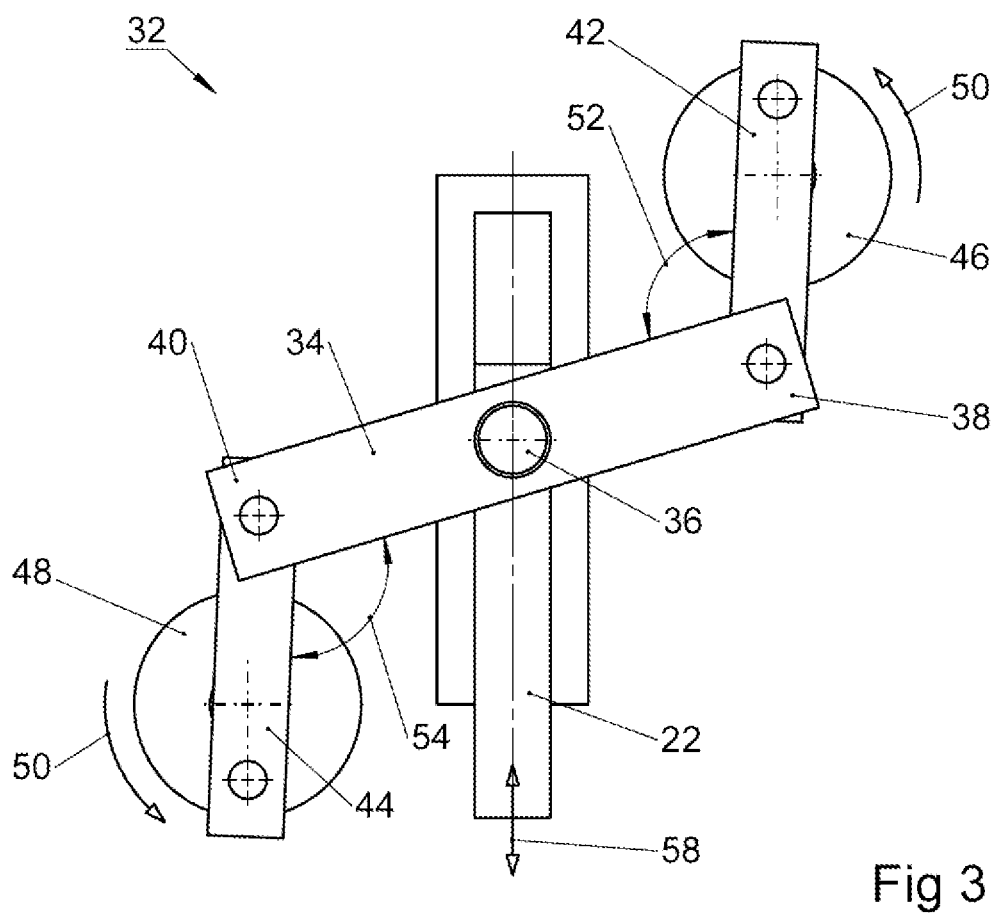
FIG. 3 shows a depiction of the principle of the drive at zero stroke.

FIG. 3 depicts the drive 32, provided in the second actuator 24, in its starting position, i.e. at zero stroke. This drive 32 has a rocker 34, in the center point 36 of which the second clamping device 22 is mounted via a flexurally soft bearing (for example by means of an elastic strip of metal) or by means of a pivot bearing. A connecting rod 42 and 44 is rotatably mounted at each of the free ends 38 and 40 of the rocker 34. The connecting rods 42 and 44 are themselves each rotatably attached to a crank mechanism 46 and 48. These crank mechanisms 46 and 48 can rotate, for example, in the direction of the arrows 50, but rotation in the opposite direction to the arrows 50 is also possible. In addition, rotation of the two crank mechanisms 46 and 48 in opposite directions is possible.

In this position of the crank mechanisms 46 and 48, which are arranged on opposite sides of the rocker 34 or point-symmetrically about the center point 36 of the rocker 34, the second clamping device 22 remains at rest (zero stroke) when the crank mechanisms 46 and 48 rotate. It should also be noted that the crank mechanisms 46 and 48 rotate simultaneously and generally at the same speed. The connecting rods 42 and 44 project from the rocker 34 in the same direction, meaning that the angles 52 and 54 are of equal size.

Figure 4:
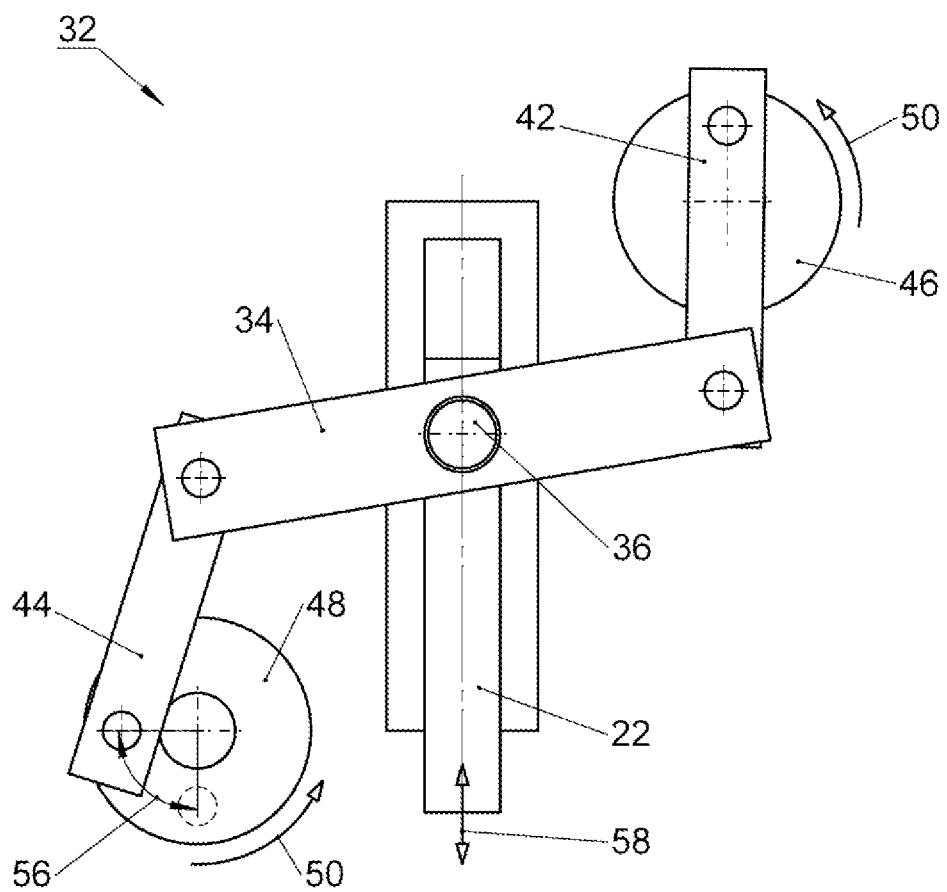
FIG. 4 shows a depiction of the principle of the drive with medium stroke.

FIG. 4 likewise shows the drive 32, but with the crank mechanism 48 rotated by 90° (angle 56) in the clockwise direction (mathematically negative). If the two crank mechanisms 46 and 48 are rotated simultaneously in this position, the second clamping device 22 completes an oscillating stroke movement 58, which is, for example, 28 mm.

Figure 5:
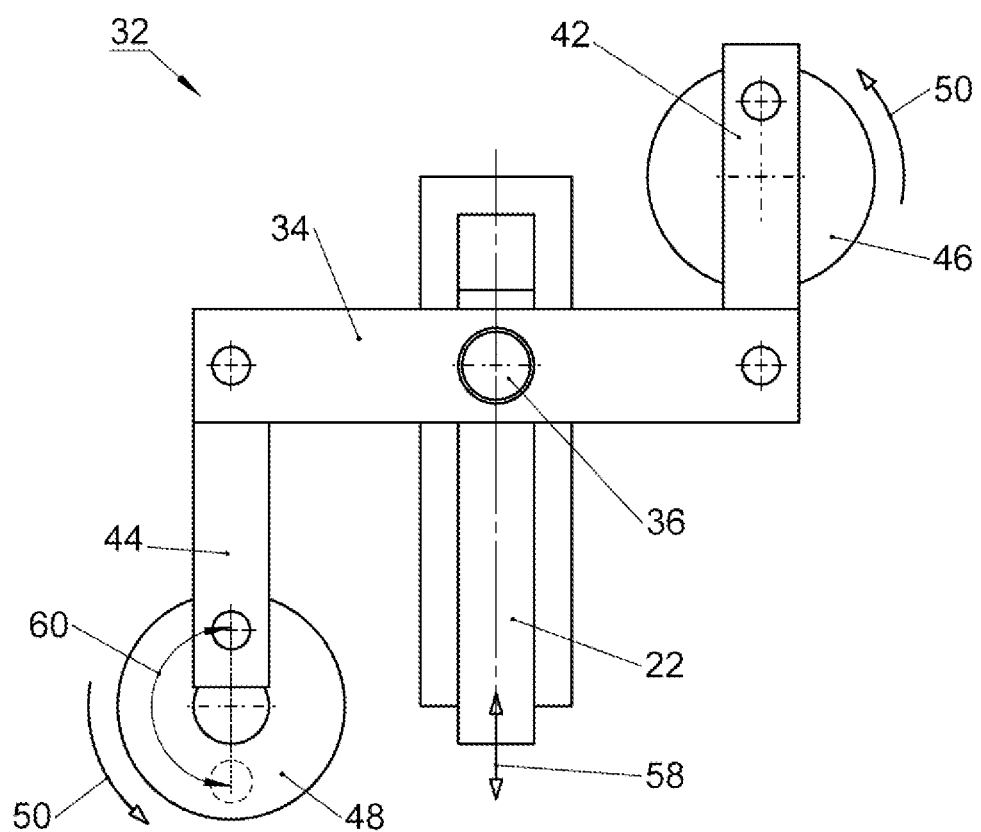
FIG. 5 shows a depiction of the principle of the drive at maximum stroke.

In FIG. 5, the crank mechanism 48 is rotated by 180° in the clockwise direction (angle 60) relative to the position shown in FIG. 3. If the two crank mechanisms 46 and 48 are now rotated (arrows 50), the second clamping device 22 again completes a stroke movement 58, but this now corresponds to a maximum stroke movement of, for example, 40 mm. It is clearly evident from FIGS. 3 to 5 that the angular adjustment of the crank mechanism 48 relative to the crank mechanism 46 enables a change in length of the stroke movement 58 to be set. In a refinement of the invention, the crank mechanism 46 may additionally also be adjusted.

Figure 6:
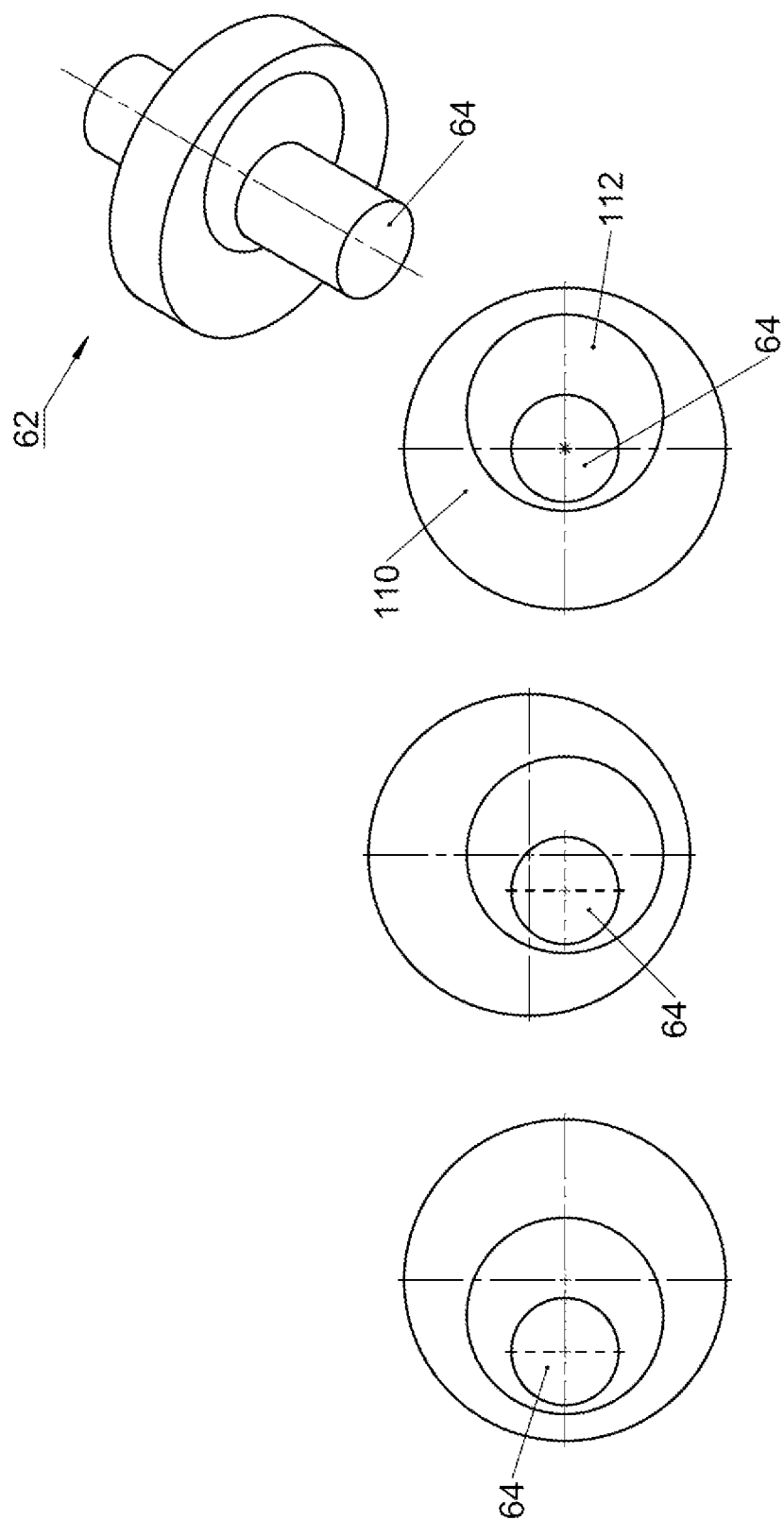
FIG. 6 shows various depictions of a twin cam.

Simple adjustment of the throw of the crank mechanism 46 or 48 can be achieved, for example, by forming the crank mechanism 46 or 48 out of a twin cam 62. FIG. 6 shows a twin cam 62 of this type in perspective view and in three cam positions. The stroke adjustment is achieved by a second cam disk 112 being accommodated in an eccentric hole of a first cam disk 110, with the journal 64 again being accommodated eccentrically in the second cam disk 112.

The cam position depicted on the left shows the maximum stroke, at which the journal 64 adopts its maximum separation from the center of the twin cam 62. In the cam position depicted on the right, the journal 64 is located precisely in the center of the twin cam. This is achieved through the first cam disk 110 being rotated through 180° and the second cam disk 112 retaining its alignment. The center depiction shows an intermediate position, in which the first cam disk 110 is rotated through 90° in an anticlockwise direction. The individual positions of the cam disks 110 and 112 and of the journal 64 can be clamped, for example, hydraulically or mechanically.

Figure 7:
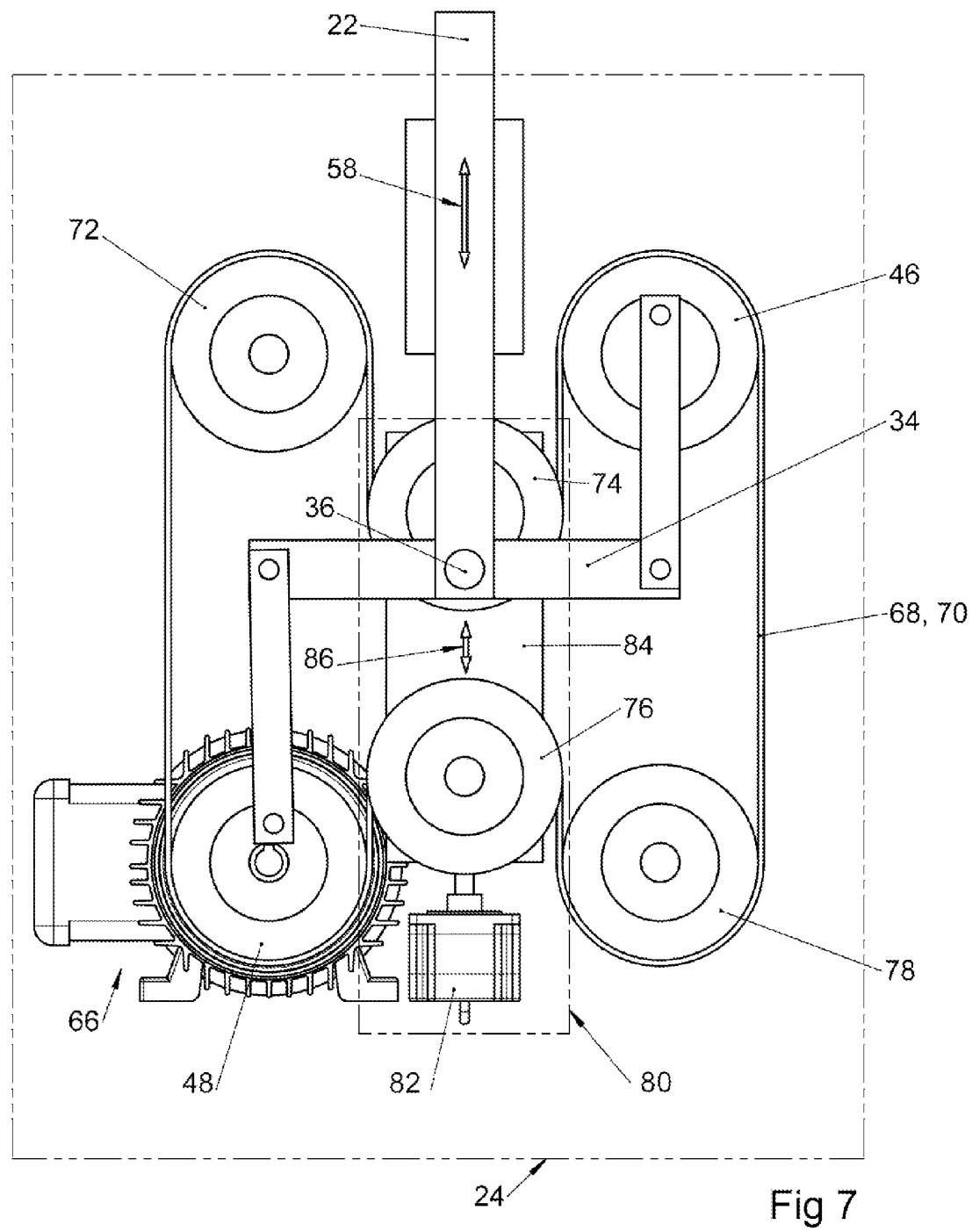
FIG. 7 shows a sketch of the principle of the drive.

In FIG. 7, 80 denotes an actuator for angular adjustment of the crank mechanism 46 and 48, and 24 denotes the second actuator for producing an oscillating stroke. Also depicted is a drive motor 66, for example a synchronous motor or a servo motor, which drives the second crank mechanism 48 directly or indirectly via a transmission. The first crank mechanism 46 is driven via a drive means 68, for example a toothed belt 70, which runs around the second crank mechanism 48 and four guide pulleys 72 to 78. The reference symbol 80 denotes an adjustment device, for example a spindle drive 82, by means of which a carriage 84 is adjusted in the direction of the arrow 86. By means of the adjustment device 80, the position of the guide rolls 74 and 76 relative to the crank mechanisms 46 and 48 is changed. Due to this change, the relative angle position of the crank mechanisms to one another is adjusted through the drawn length of the drive means between the two crank mechanisms 46 and 48 being shortened or lengthened. Since the two guide pulleys 74 and 76 are adjusted simultaneously when the carriage 84 is displaced, the drive means' length in the arrangement shown does not change in the case of an adjustment, and there is no need to regulate the tension of the drive means 68 owing to changed positions of the guide rolls 74 and 76.

Figure 8:
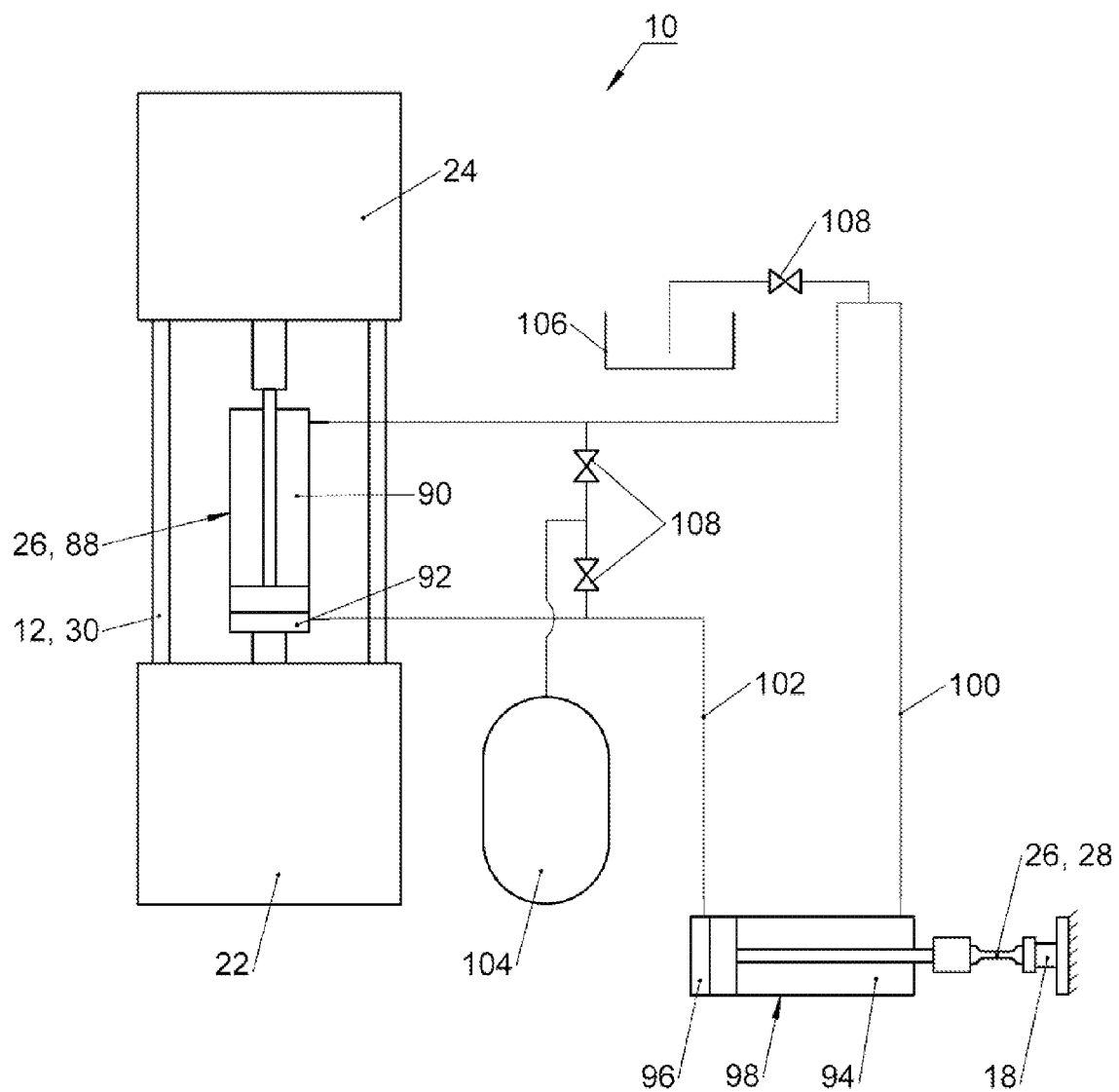
FIG. 8 shows a further variant of the test device according to the invention.

FIG. 8 depicts a third variant of the test device according to the invention, in which the workpiece 26 is in the form of a hydraulic cylinder 88. The pressure chambers 90 and 92 of the hydraulic cylinder 88 are connected to pressure chambers 94 and 96 of a second hydraulic cylinder 98 by means of hydraulic lines 100 and 102. The second hydraulic cylinder 98 acts on a sample 28 and transfers the stroke movements produced in the first hydraulic cylinder 88. This enables, for example, poorly accessible or very large samples 28 to be tested. Furthermore, a pressure accumulator 104 and a tank 106 are evident in FIG. 8. The connections to the pressure accumulator and to the tank 6 can be blocked by means of magnetic valves 108.

What is claimed is:

1. A test device (10) for the static and dynamic testing of workpieces (26), the test device (10) having a first clamping device (20) and a second clamping device (22) for the workpiece (26), and a drive (32) for moving the second clamping device (22), characterized by the drive (32):
    a) having a rocker (34) on which the second clamping device (22) is rotatably mounted;
    b) the two ends of the rocker (34) each being connected to a rotatably mounted connecting rod (42, 44); and
    c) the free ends of the connecting rods (42, 44) each being coupled to a crank mechanism (46, 48), said crank mechanisms (46, 48) being arranged on opposite sides of the rocker (34) and arranged so that the connecting rods (42, 44) project from the ends of the rocker (34) in the same direction when said crank mechanisms (46, 48) are set in the starting position at zero stroke and when viewed from the center point of the rocker (34) in the direction of the ends thereof.

2. The test device according to claim 1, characterized in that the second clamping device (22) is rotatable mounted at the center point (36) of the rocker (34).

3. The test device according to claim 1, characterized in that the second clamping device (22) is connected to the rocker (34) at the center point (36) thereof by means of a flexurally soft bearing.

4. The test device according to claim 1, characterized in that the two connecting rods (42, 44) are connected to the ends of the rocker (34) by means of a flexurally soft bearing.

5. The test device according to claim 1, characterized in that the crank mechanisms (46, 48) each has an adjustable cam.

6. The test device according to claim 5, characterized in that the crank mechanism (46, 48) comprises a twin cam (62).

7. The test device according to claim 1, characterized in that the crank mechanisms (46, 48) rotate in the same or opposite directions.

8. The test device according to claim 1, characterized in that the crank mechanisms (46, 48) can each be driven at the same speed by their own electric motor (66), where the desired relative angular position of the two crank mechanisms (46, 48) can be adjusted by precise phase regulation of the electric motors (66).

9. The test device according to claim 1, characterized in that the crank mechanisms (46, 48) can each be driven at different speeds by their own electric motor (66), where successive strokes differ in amplitude.

10. The test device according to claim 1, characterized in that the crank mechanisms (46, 48) are connected to one another by a drive means (68, 70), where the length of the section of the drive means (68, 70) under tension between the two crank mechanisms (46, 48) can be adjusted by a change in the position of guide rolls (74, 76), which in turn has the consequence of a change in the angular position of the crank mechanisms (46, 48) with respect to one another.

11. The test device according to claim 10, characterized in that the carriage (84) can be moved mechanically by means of a threaded spindle (82), hydraulically or pneumatically, and the position of the guide rolls (74, 76) is thus changed.

12. The test device according to claim 1, characterized in that the first clamping device (20) is additionally connected to a quasi-statically acting actuator (14), which is suitable for achieving displacement of the workpiece (26) relative to a second actuator (24) and thus producing a prestress of the workpiece (26).

13. The test device according to claim 1, characterized in that a cyclic drive (32) is integrated into a dynamic actuator unit (24), and a quasi-statically acting actuator (14) is rigidly connected to the dynamic actuator unit (24), so that the static actuator (14) changes the position of the dynamic actuator unit (24) so as to produce a prestress of the workpiece (26) on which the cyclic strokes of the dynamic actuator unit (24) are superimposed.

14. The test device according to claim 1, characterized in that a sample (28) or a hydraulic cylinder (88) is clamped in for the workpiece (26).

15. The test device according to claim 14, characterized in that a hydraulic cylinder (88) hydraulically drives an externally arranged second hydraulic cylinder (98).

16. The test device according to claim 1, characterized in that a plurality of test devices (10) are simultaneously used synchronously or intentionally asynchronously and act on a workpiece (26) or a sample (28) through electronic synchronization of the drives (32).

\* \* \* \* \*